(12) United States Patent
Oslick et al.

(10) Patent No.: US 6,967,031 B1
(45) Date of Patent: Nov. 22, 2005

(54) COMPOSITIONS FOR PREVENTION AND TREATMENT OF SYMPTOMS ASSOCIATED WITH ETHYL ALCOHOL CONSUMPTION

(76) Inventors: Brian Douglas Oslick, 1803 Shepherd Ct. Suite 107, Waukesha, WI (US) 53186; Donald Barclay, 1235 W. Barry Unit B, Chicago, IL (US) 60657

( * ) Notice: Subject to any disclaimer, the term of this patent is extended or adjusted under 35 U.S.C. 154(b) by 0 days.

(21) Appl. No.: 11/005,261

(22) Filed: Dec. 7, 2004

Related U.S. Application Data

(62) Division of application No. 10/368,942, filed on Feb. 18, 2003.

(51) Int. Cl.⁷ ............................................. A61K 35/78
(52) U.S. Cl. ...................... 424/725; 424/682; 424/646; 424/638; 514/52; 514/159
(58) Field of Search ................. 424/725, 682, 424/646, 638; 514/52, 159

(56) References Cited

U.S. PATENT DOCUMENTS

| | | |
|---|---|---|
| 4,496,548 A | 1/1985 | Moldowan et al. |
| 5,324,516 A | 6/1994 | Pek et al. |
| 5,712,309 A | 1/1998 | Finnin et al. |
| 5,804,596 A | 9/1998 | Majeed et al. |
| 5,968,520 A | 10/1999 | Nam et al. |
| 6,077,838 A | 6/2000 | Hausheer |
| 6,312,736 B1 | 11/2001 | Kelly et al. |
| 2001/0000472 A1 | 4/2001 | Henderson et al. |
| 2001/0043956 A1 | 11/2001 | Mirza et al. |
| 2002/0006910 A1 | 1/2002 | Miasnikov et al. |
| 2002/0102237 A1 | 8/2002 | Hammerly |

FOREIGN PATENT DOCUMENTS

| | | |
|---|---|---|
| EP | 1 021 198 B1 | 7/2000 |
| WO | WO 99/18985 | 4/1999 |
| WO | WO 00/71145 A1 | 11/2000 |
| WO | WO 02/05831 A1 | 1/2002 |
| WO | WO 02/34275 A1 | 5/2002 |

OTHER PUBLICATIONS

Walter H. Schmitt Jr et al., "The Art of Getting Well Molybdenum for Candida albicans Patients and Other Problems" pp. 1-9; 1991.

*Primary Examiner*—Susan D. Coe

(57) ABSTRACT

Described is a composition for the prevention and treatment of symptoms associated with ethyl alcohol consumption. The composition comprises silymarin, salicin, at least one B vitamin, magnesium, molybdenum and manganese. Treatment of symptoms associated with the consumption of ethyl alcohol involves ingesting the described composition prior to, during, or after the consumption of the alcohol.

8 Claims, No Drawings

COMPOSITIONS FOR PREVENTION AND TREATMENT OF SYMPTOMS ASSOCIATED WITH ETHYL ALCOHOL CONSUMPTION

This application is a divisional application of U.S. patent application Ser. No. 10/368,942, filed Feb. 18, 2003, pending.

FIELD OF THE INVENTION

The invention relates to compositions and methods for prevention or treatment of negative effects of consuming ethyl alcohol in the form of alcoholic beverages. The composition can be used in the form of a nutritional supplement and the treatment may be administered prior to, during, or after the consumption of ethyl alcohol.

BACKGROUND OF THE INVENTION

The consumption of ethyl alcohol may be followed by a syndrome known as hangover. Symptoms of a hangover include headache, dehydration, nausea, nerve and muscle pain, lethargy, congestion, chills, tremor, diarrhea and fever. These symptoms may be particularly severe, especially after heavy consumption of alcoholic drinks. While not life-threatening, these symptoms are unpleasant and may interfere with job performance or home life. Additionally, the condition of alcohol induced hangover may cause a person to suffer a social stigma associated with the condition.

Ethyl alcohol, or ethanol, is typically consumed by ingesting a liquid containing ethyl alcohol is typically produced by yeast in a fermentation process which converts sugars to alcohol and is then consumed, as is, in the case of beer or wine, for example. The fermented alcohol may be distilled to form spirits and then consumed, as is, in the case of vodka, for example. Additional sweeteners, water and other ingredients may be added. Once consumed; the ethyl alcohol in the beverage is absorbed by the stomach or small intestine and transferred to the liver through blood vessels. Metabolism of the alcohol takes place in a two-step enzymatic reaction. First, the alcohol is oxidized to acetaldehyde by alcohol dehydrogenases. Second, the acetaldehyde is oxidized to acetic acid by acetaldehyde dehydrogenases. The acetic acid is transported to the muscles and adipose tissue where it will be further broken down into carbon dioxide and water. The rate at which alcohol is metabolized depends upon the level of presence and activity of these enzymes. The rate at which alcohol is metabolized and eliminated from the body varies greatly among individuals.

The negative effects of consumption of ethanol are due mainly to the toxic effects of acetaldehyde. Acetaldehyde provokes disturbances in bodily processes by, for example, forming adducts with hemoglobin and proteins of plasma of the brain and other organs; and inhibiting the transfer of reducing agents along the mitochondrial respiratory chain. Acetaldehyde also accumulates in the cerebellum causing headache by contracting cerebral blood vessels thereby decreasing blood flow resulting in pain.

The symptoms of hangover have been treated with painkillers, such as aspirin or non-steroid anti-inflammatory drugs ("NSAIDs") or antacids. However, painkillers may cause additional stomach upset and do not, alone, treat other symptoms of hangover. Acetaminophen, which is neither aspirin nor an NSAID, has been used to treat headaches and pains associated with hangover, but acetaminophen in combination with ethanol can result in extensive liver damage. The diuretic effect of alcohol results in dehydration and is generally treated with the consumption of large amounts of water after drinking ethanol. The consumption of water after drinking alcohol, however, does not alleviate the problems associated with the build up of acetaldehyde in the liver.

Other means for treating hangover symptoms include "hair-of-the-dog" type treatments involving additional ethyl alcohol consumption for its analgesic properties. Such remedies ultimately prolong the effects of overindulgence, are dangerous and may lead to alcohol addiction.

Herbal remedies have been used to alleviate or prevent symptoms of hangover. Examples of herbal remedies include teas made from the extracts of leaves, stems or roots of alder or mountain ash. This tea is rich in tannin that is said to provide protection to the stomach mucosa. Extracts of fruits of other plants may be added to the teas for their Vitamin C, amino acids and beta-carotene content. The beta-carotene is effective at clearing up cough and phlegm.

Ginkgo biloba extract and taurine are components of another composition that has been used to alleviate hangover symptoms. The taurine is taken for liver protection and the Ginkgo biloba for its antioxidant effects against ethanol-derived oxidation and also facilitates circulation in the brain.

Several methods of preventing alcohol absorption or allaying drunkenness are known. Abstinence, charcoal ingestion and charcoal ingestion in combination with Vitamin B-6 and Ephedra are examples. By abstaining from the consumption of alcoholic beverages a person avoids absorption of any ethanol and subsequent build up of acetaldehyde in the liver. However, the abstainer also will not enjoy the intoxicating effects of alcohol consumption. Charcoal ingestion is intended to absorb the alcohol in the stomach or small intestines resulting in a lower blood alcohol level. Charcoal ingestion therefore will decrease the socially desired effects associated with the consumption of ethanol. The Ephedra in the combination of Ephedra, charcoal and Vitamin B-6, acts as a vasoconstrictor of blood vessels, a stimulant, and a bronchiodialator. Galenic compositions have also been used to decrease the amount of blood alcohol. Another method of allaying drunkenness has been to ingest a combination of succinic acid, an L-glutamate compound, a fumaric acid compound, ascorbic acid, an energizer and a sugar. This method is also intended to dampen the intoxicating effects of alcohol consumption as well as treat the negative symptoms.

There is a need for compositions and preventative treatments for ethanol induced hangover symptoms that are effective at treating the various symptoms of hangover without aggravating the symptoms further. Further, there is a need for the compositions and treatments for hangover symptoms to allow the user to enjoy the desired social effects of ethanol consumption while treating the cause of the negative effects of alcohol consumption.

The invention provides a composition and method for preventing or treating ethanol induced hangover symptoms while avoiding the worsening of symptoms. These compositions and methods also allow for the enjoyment of the desired social effects of ethanol while preventing or treating the negative effects of ethanol consumption.

BRIEF SUMMARY OF THE INVENTION

One embodiment of the invention is a composition comprising silymarin, salicin, at least one B vitamin, magnesium, molybdenum and manganese. In one form of the composition, the at least one B vitamin is a combination of folic acid, Vitamin B12 and Vitamin B6.

In one embodiment, the silymarin is soluble and in another embodiment the silymarin is a methylglucamine salt of silymarin.

Another embodiment is a beverage comprising the composition of silymarin, salicin, at least one B vitamin, magnesium, molybdenum, manganese and a sweetener. In other embodiment, the beverage comprises the composition of silymarin, salicin, at least one B vitamin, magnesium, molybdenum, manganese and natural or artificial flavors.

In yet a further embodiment of the invention, a method is provided for decreasing the negative effects of ethyl alcohol consumption comprising the step of administering to a person an amount of the composition sufficient to decrease the effects of acetaldehyde build up.

Further, alternate embodiments include practicing the method prior to, simultaneously with or subsequent to the ingestion of ethyl alcohol.

DETAILED DESCRIPTION OF THE INVENTION

The composition of the present invention comprises essentially silimarin, salicin, B vitamins, magnesium, molybdenum and manganese. The composition may be administered before, during or after the consumption of ethanol to prevent or treat the negative effects of ethanol consumption while allowing the consumer of ethanol to enjoy the pleasant social effects of the alcohol.

The terms "ethyl alcohol" and "ethanol" as used herein refer to any ethyl alcohol containing, or alcoholic, beverage including beer, wine, spirits and the like.

Silymarin is a compound contained in a plant named Milk thistle (Silybum marianum) and is commonly known as St. Mary's thistle and Our Lady's thistle. Silymarin consists of various forms of hepatoprotectant flavonolignins. Silymarins protect the liver against a variety of toxins. The active components in silymarin include silybin, silychristin and silydianin. Silymarin repair mechanisms include increased synthesis of cellular proteins, increased rate of hepatocellular repair and anti-oxidant activity. Silymarin contributes to the regenerative activity of the liver by stimulating RNA polymerase and increasing synthesis of ribosomes.

Silybins are only partially soluble in aqueous environments such as the body. Aqueous solutions of the compositions described herein are preferred for their increased bioavailability of silybins. The solubility of silybins is increased by forming salts of the compound or by chelation forming salt like compounds. Salts of silymarin extract have greater aqueous solubility and therefore greater bioavailability. One such salt of silymarin is an esterified hemisuccinate salt of silymarin. In particular, methylglucamine salt of silymarin is preferred for increased aqueous solubility and bioavailability. Chelation between methylglucamine and silymarin forms a salt. The methylglucamine salt of silymarin is available from Infinity Industries, Inc. (Ronkonkoma, N.Y.), as are all ingredients of the compositions described herein.

The bioavailability of silymarin may also be increased by preparing a fluid mixture of Milk thistle dry extract in polyethylene glycol as described in EP 1 021 198 B 1.

Concentrations or methylglucamine salt of silymarin in the range of from about 1.3 to about 27 percent by weight are used in the composition to alleviate hangover symptoms. A preferred concentration is about 3.6% by weight.

Salicin is a compound contained in a plant known as Willow Bark or White Willow Bark. The extract of Willow Bark contains salicinium which reduces headache pain. The pain-relieving effects of salicin are similar to those of aspirin without side effects such as stomach upset. Salicin is converted to aspirin in vivo and provides a delayed pain relieving affect after the ingestion of the compositions disclosed herein. Therefore, stomach upset is delayed or may not be perceived due to the pain relieving effects of the alcohol ingested. Salicin's inhibitory effect on prostaglandin synthesis in nerve cells is the mechanism by which salicin relieves pain. White willow bark extract or pure salicin in the concentration range of from about 1.5 to about 21 percent by weight are used in the compositions described herein to provide relief from hangover symptoms. A concentration of about 4.5% is preferred.

B vitamins combat the depressive effects of ethanol consumption, particularly vitamins B12 and folic acid. Vitamin B6, in addition to combating depression, also assists in the transmission of chemicals in the nervous system. B vitamins are lost during the consumption of ethanol due to the diuretic effects of such consumption. It is preferred to use vitamins B6, B12 and folic acid in combination as these vitamins in combination increase levels of tetrahydropterin, a coenzyme necessary for the production of serotonin (and thus melatonin), dopamine, epinephrine and norepinephrine. A concentration of vitamin B6 in the range of from about 0.12 to about 2.05 percent by weight is used in the composition and a concentration of about 0.36% by weight is preferred. Concentrations of folic acid of from about 0.05 to about 0.8 percent by weight are used and a concentration of about 0.14% by weight is preferred. Concentrations of vitamin B12 of from about 0.06 to about 1.03 are used and a preferred concentration is about 0.18% by weight.

Magnesium is a component of red blood cells and plays role in controlling blood pressure. Maintaining control of blood pressure is a factor in controlling the severity of a headache. Magnesium may be included in the compositions disclosed herein the forms of magnesium citrate in concentrations of from about 55% to about 97.45% by weight and preferably about 90% by weight.

Molybdenum acts as a co-factor of aldehyde dehydrogenase in the oxidation process that results in the conversion of alcohol to acetic acid. Specifically, molybdenum assists the enzyme aldehyde oxidase or aldehyde dehydrogenase in acetaldehyde to acetic acid. Molybdenum also alleviates the allergenic effects of aldehydes or ketones in persons sensitive to these compounds. Molybdenum may be added to the compositions disclosed herein in the form of chelated molybdenum in concentrations that from about 0.03% to about 1.03% by weight and preferably about 0.18% by weight.

Manganese directly oxidizes acetaldehyde to acetic acid and therefore quickens the alleviation of negative symptoms caused by acetaldehyde build up after the consumption of ethanol. Aldehyde dehydrogenase enzyme may use manganese as a cofactor instead of molybdenum. Preferred manganese compounds exhibit the lowest oxidation state (+2). The Manganese may be added to the compositions disclosed herein in the form of manganese sulfate in concentrations that range from about 0.3% to about 5% by weight and preferably about 0.9% by weight.

The formulations described herein may be administered by any appropriate means. The preferred means of administration is by oral route. The formulation may be ingested in pill, tablet, capsule or liquid form. The liquid form is preferred for its higher bioavailibity of silymarin. Effective amounts of the compositions may be administered before or after the consumption of an alcoholic beverage, preferably before the consumption of alcohol so that the active components are available when acetaldehyde levels begin to build. The compositions may be administered during the consumption of alcohol alone or in combination with a specific ethanol as a drink mixer.

The compositions may be self-administered and the amount required to be taken is dependent upon several factors regarding the person ingesting the ethanol. The amount, type and strength of the alcoholic beverage the person intends to consume, knowledge of ethanol tolerance of the person and the need for alertness and/or focus for activities that will follow consumption of such beverages are factors considered when determining dose.

Subjective tests were conducted by asking individuals who used the compositions described herein before during and after the consumption of alcoholic beverages how they felt after consuming several alcoholic drinks. The following compositions offered noticeable relief to the negative effects to alcohol consumption:

20–150 mg of silymarin methylglucamine (1.23–35.81 wt %);
10–75 mg salicin (0.59–21.17 wt %);
2–6 mg of Vitamin B6 (0.11–2.05 wt %);
0.8–2.4 mg folic acid (0.03–0.83 wt %);
1–3 mg Vitamin B12 (0.05–1.03 wt %);
250–1500 mg of magnesium citrate (49.56–97.45 wt %);
0.5–3 mg of chelated molybdenum (0.03–1.03 wt %); and
5–15 mg of manganese sulfate (0.29–5.01 wt %)

Preferred ranges of the individual components of the composition are:

20–60 mg of silymarin methylglucamine (1.23–10.09 wt %);
25–75 mg salicin (1.55–21.17 wt %);
2–6 mg of Vitamin B6 (0.11–2.05 wt %);
0.8–2.4 mg folic acid (0.05–0.83 wt %);
1–3 mg Vitamin B12 (0.06–1.03 wt %);
500–1500 mg of magnesium citrate 75.26–97.45 wt %);
1–3 mg of chelated molybdenum (0.06–1.03 wt %); and
5–15 mg of manganese sulfate (0.29–5.01 wt %)

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While some potential advantages and objects have been expressly identified herein, it should be understood that some embodiments of the invention may not provide all, or any, of the expressly identified advantages and objects.

Preferred embodiments of this invention are described herein, including the best mode known to the inventors for carrying out the invention. Of course, variations of those preferred embodiments will become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The following examples further illustrate the invention but, of course, should not be construed as in any way limiting its scope.

Example 1 includes the following formulation (values are in wt %):

| | |
|---|---|
| silymarin methylglucamine | 9.94 |
| salicin | 16.75 |
| Thiamine HCL | 1.23 |
| Riboflavin | 1.68 |
| Niacinamide | 1.68 |
| pantothenic acid | 0.84 |
| Vitamin B6 | 0.17 |
| folic acid | 0.03 |
| Vitamin B12 | 0.05 |
| Chelated molybdenum | 0.03 |
| magnesium citrate | 67.15 |
| manganese sulfate | 0.45 |

What is claimed is:

1. A method for decreasing the negative effects of ethyl alcohol consumption, the method comprising the step of administering to a person an amount of a composition comprising:
   a silymarin;
   salicin;
   at least one B vitamin;
   magnesium;
   molybdenum; and
   manganese.

2. The method of claim 1 wherein the composition is administered prior to the ingestion of ethyl alcohol.

3. The method of claim 1 wherein the composition is administered simultaneously with the ingestion of ethyl alcohol.

4. The method of claim 1 wherein the composition is administered subsequent to the ingestion of ethyl alcohol.

5. The method of claim 1 wherein the silymarin is silymarin methylglucamine.

6. The method of claim 5 wherein the silymarin methylglucamine is present in a range of about 1.3 to about 27 percent by weight of the total composition; the salicin is present in a range of from about 1.5 to about 21 percent by weight; the at least one B vitamin is present in a range of from about 0.05 to about 2.05 percent by weight; the magnesium is present in a range of from about 55 to about 97.45 percent by weight; the molybdenum is present in a range of from about 0.3 to about 1.03 percent by weight; and the manganese if present in a range of from about 0.03 to about 5.0 percent by weight of the total composition.

7. The method of claim 1 wherein the at least one B vitamin is a combination of folic acid, Vitamin B12 and Vitamin B6.

8. The method of claim 1 wherein the silymarin is soluble.

* * * * *